(12) United States Patent
Motoyama et al.

(10) Patent No.: US 7,160,701 B2
(45) Date of Patent: Jan. 9, 2007

(54) GENES FOR DETECTING BACTERIA AND A METHOD FOR DETECTING BACTERIA BY USING THE GENES

(75) Inventors: Yasuo Motoyama, Moriya-machi (JP); Tomoo Ogata, Moriya-machi (JP); Kazuhisa Sakai, Moriya-machi (JP)

(73) Assignee: Asahi Breweries, Ltd., Tokyo (JP)

( * ) Notice: Subject to any disclaimer, the term of this patent is extended or adjusted under 35 U.S.C. 154(b) by 474 days.

(21) Appl. No.: 10/600,642

(22) Filed: Jun. 23, 2003

(65) Prior Publication Data

US 2004/0018537 A1    Jan. 29, 2004

Related U.S. Application Data

(62) Division of application No. 09/762,633, filed as application No. PCT/JP99/04341 on Aug. 11, 1999, now Pat. No. 6,632,642.

(30) Foreign Application Priority Data

Aug. 11, 1998 (JP) ............................. 10/227177

(51) Int. Cl.
*C12P 19/34* (2006.01)

(52) U.S. Cl. ............... 435/91.2; 435/6; 536/24.32; 536/24.3; 536/23.1

(58) Field of Classification Search .................. None
See application file for complete search history.

(56) References Cited

U.S. PATENT DOCUMENTS 5,869,642 A * 2/1999 Sakamoto ............ 536/24.31

OTHER PUBLICATIONS

Kim, et al., Gene. Complete sequences and organization of the rrnA operon form Campylobacter jejuni TGH9001. vol. 164, No. 1, pp. 101-106. 1995.

* cited by examiner

*Primary Examiner*—Juliet C. Switzer
(74) *Attorney, Agent, or Firm*—Browdy and Neimark, PLLC

(57) ABSTRACT

The present invention relates to genes for detecting the genus *Pectinatus frisingensis* or *Pectinatus cerevisiiphilus* of the genus *Pectinatus*, which is known as beer-spoilage bacteria, and a method for detecting the bacteria by 5 using the genes. The present invention provides gene sequences of spacer regions between 16S rRNA genes and 23S rRNA genes specific for the genus *Pectinatus* relating to beer-spoilage and a method for quickly and sensitively detecting the bacteria by using the sequences.

7 Claims, 1 Drawing Sheet

GENES FOR DETECTING BACTERIA AND A METHOD FOR DETECTING BACTERIA BY USING THE GENES

CROSS-REFERENCE TO RELATED APPLICATIONS

This application is a divisional application of Ser. No. 09/762,633, filed Feb. 12, 2001 now U.S. Pat. No. 6,632, 642, which is the National Phase under 35 USC 371 of PCT/JP99/04341 filed Aug. 11, 1999.

FIELD OF THE INVENTION

The present invention relates to genes for detecting *Pectinatus frisingensis* or *Pectinatus cerevisiiphilus* of the genus *Pectinatus*, which is known as beer-spoilage bacteria, and a method for detecting the bacteria by using the genes.

DESCRIPTION OF THE PRIOR ART

Bacteria of the genus *Pectinatus* have been known as beer-spoilage bacteria. In the genus, two kinds of *Pectinatus frisingensis* and *Pectinatus cerevisiiphilus* have been known. For detecting the bacteria of the genus *Pectinatus*, the bacteria must be isolated after multiplication culture and separation culture. It takes at least seven days. Then, isolated bacteria are multiplied and tested by many qualitative tests such as morphological observation, gram stainability, a catalase test, utilization of various carbon sources and the like to identify the bacteria.

These tests are very troublesome, and it takes much time and it costs much. In addition to these common identification tests, there is a method that DNA is extracted from isolated bacteria, fixed on a membrane, and conducted a hybridization test by using standard bacteria DNA as a probe to identify the class. However, it takes some days, and it is difficult to obtain necessary detective sensitivity and selectivity.

Lately, a method for detection of bacteria of the genus *Pectinatus* is disclosed by using a monoclonal antibody that specifically reacts with *Pectinatus cerevisiiphilus* (ASBC Journal: 51(4)158–163, 1993). However, the method is insufficient to the detective sensitivity. The method has a problem that *Pectinatus frisingensis* can not be detected.

The other detection method has been reported. It can detect *Pectinatus frisingensis* and *Pectinatus cerevisiiphilus* by a Ribotyping method that polymorphism of a ribosomal RNA gene is detected (J. Am. Soc. Chem.: 56 (1) 19–23, 1998). However, since the method needs operation for isolating the bacteria, it has problems of detective sensitivity and speed.

Considering these problems, further quick detection methods have been studied. WO97/20071 discloses a method for detecting *Pectinatus* comprising extracting DNA of the test microorganism, and using a PCR method that a complementary oligonucleotide of the DNA functionates as a primer. However, the base sequences of 16S rRNA gene used in the technique are sometimes similar to those of microorganisms of the other genera, so that there are problems that the other microorganisms are detected in addition to particular microorganisms to be detected.

The gene in a spacer between a 16S rRNA gene and a 23S rRNA gene has a specific gene sequence. Though methods for detecting microorganisms using the gene sequence are disclosed in Japanese Jozo Ronbunshu 50, 22–31 (1995), APPL. ENVIRON. MICROBIOL. VOL.62, NO.5, 1683–1688(1996), FEMS MICROBIOL LETT. VOL. 84, NO.3, 307–312 (1991), Japanese Patent Kokai Publication No. 6-98800 and the like, gene sequences of the spacers of the genus *Pectinatus* have not been found.

SUMMARY OF THE INVENTION

The present invention aims to provide gene sequences of a spacer region that is constituted between a 16S rRNA gene and a 23S rRNA gene specific for the genus *Pectinatus* relating to beer-spoilage, and to provide a method for sensitively and quickly detecting the genus by using the sequences.

(1) The first invention is a gene sequence of a spacer region between a gene coding 16S rRNA and a gene coding 23S rRNA of *Pectinatus frisingensis* containing a part of the base sequence or the whole base sequence represented by SEQ ID NO: 1.

(2) The second invention is a gene sequence of a spacer region between a gene coding 16S rRNA and a gene coding 23S rRNA of *Pectinatus frisingensis* containing a part of the base sequence or the whole base sequence represented by SEQ ID NO: 2.

(3) The third invention is a gene sequence of a spacer region between a gene coding 16S rRNA and a gene coding 23S rRNA of *Pectinatus cerevisiiphilus* containing a part of the base sequence or the whole base sequence represented by SEQ ID NO: 3.

(4) The fourth invention is a gene sequence of a spacer region between a gene coding 16S rRNA and a gene coding 23S rRNA of *Pectinatus cerevisiiphilus* containing a part of the base sequence or the whole base sequence represented 10 by SEQ ID NO: 4.

(5) The fifth invention is an oligonucleotide characterized in that the gene sequence of a spacer region between a gene coding 16S rRNA and a gene coding 23S rRNA of *Pectinatus frisingensis* has at least one of the following sequence group or the corresponding complementary sequence:

5'-CCATCCTCTTGAAAATCTC-3' ① (SEQ ID NO:5)
5'-TCTCYTCTCACAAGTTTGGC-3' ② (SEQ ID NO:6).

| 5'-CCATCCTCTTGAAAATCTC-3' | ① | (SEQ ID NO:5) |
| 5'-TCTCYTCTCACAAGTTTGGC-3'. | ② | (SEQ ID NO:6) |

(6) The sixth invention is an oligonucleotide characterized in that the gene sequence of a spacer region between a gene coding 16S rRNA and a gene coding 23S rRNA of *Pectinatus cerevisiiphilus* has at least one of the following sequence group or the corresponding complementary sequence:

| 5'-CACTCTTACAAGTATCTAC-3' | ③ | (SEQ ID NO:7) |
| 5'-CCACAATATTTCCGACCAGC-3' | ④ | (SEQ ID NO:8) |
| 5'-AGTCTTCTCTACTGCCATGC-3' | ⑤ | (SEQ ID NO:9) |

(7) The seventh invention is a method for detecting *Pectinatus frisingensis*, wherein the oligonucleotide made from the gene sequence described in (1) or (2) uses as a primer for synthesis of nucleic acids, and the nucleic acid is treated by gene amplification to detect the bacteria.

(8) The eighth invention is a method for detecting *Pectinatus cerevisiiphilus*, wherein the oligonucleotide made from the gene sequence described in (3) or (4) uses as a primer for synthesis of nucleic acids, and the nucleic acid is treated by gene amplification to detect the bacteria.

(9) The ninth invention is a method for detecting *Pectinatus frisingensis*, wherein the oligonucleotide made from the gene sequence described in (1) or (2), or the oligonucleotide made from the gene sequence described in (5), and a nucleotide sequence coding 16S rRNA gene of *Pectinatus frisingensis* use as primers for synthesis of nucleic acids, and the nucleic acid is treated by gene amplification to detect the bacteria.

(10) The tenth invention is a method for detecting *Pectinatus cerevisiiphilus*, wherein the oligonucleotide made from the gene sequence described in (3) or (4) or the oligonucleotide made from the gene sequence described in (6), and a nucleotide sequence coding 16S rRNA gene of *Pectinatus cerevisiiphilus* use as primers for synthesis of nucleic acids, and the nucleic acid is treated by gene amplification to detect the bacteria.

(11) The eleventh invention is a method as in (9), wherein the nucleotide sequence coding the 16S rRNA gene of *Pectinatus frisingensis* has the following sequence:

5'-CGTATCCAGAGATGGATATT-3' ⑥ (SEQ ID NO:10)

(12) The twelfth invention is a method as in (10), wherein the nucleotide sequence coding the 16S rRNA gene of *Pectinatus cerevisiiphilus* has the following sequence:

5'-CGTATGCAGAGATGCATATT-3' ⑦ (SEQ ID NO:11)

DETAILED DESCRIPTION OF THE INVENTION

Figure 1:
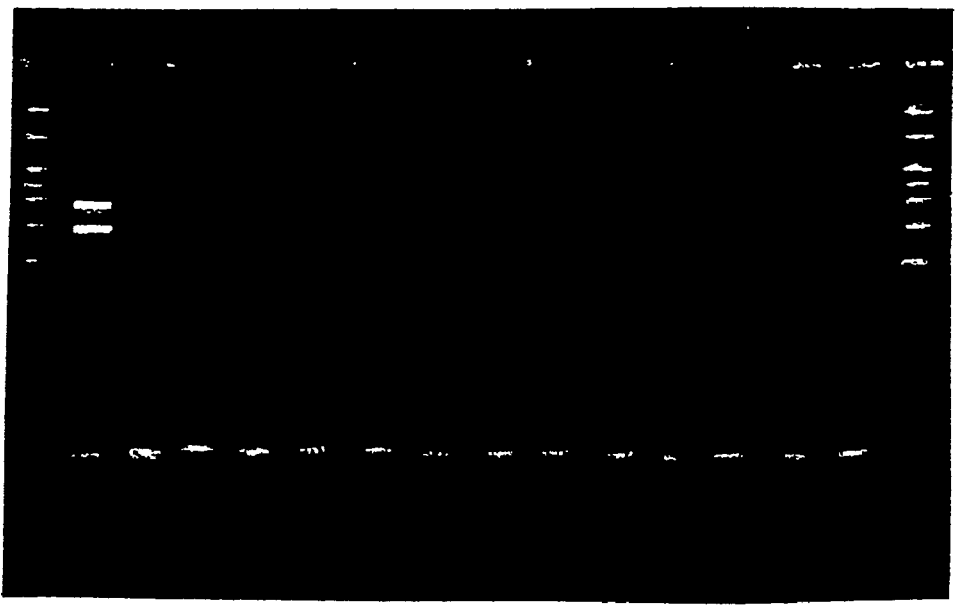
FIG. 1. It shows Electrophoretogram in Example 3.

Since the technique of gene amplification is well known, it is conducted under the polymerase chain reaction method which has been developed by Saiki et al. (abbreviated as PCR method hereinafter; Science 230, 1350, 1985).

This method is conducted by amplification reaction of particular gene sequences. Since the method shows quick reaction, high sensitivity and specificity and convenience, applications has been tried to quickly judge viruses in medical fields or quickly detect noxious bacteria in food fields. By the PCR method, even if only a few nucleotide sequences are present in test samples, the target nucleotide sequence between two primers is amplified several hundred times, and the copies are produced in large quantities to be detectable. For conducting the PCR method, the nucleic acid ingredient should be liberated from the bacteria in the test samples. However, in the PCR method, when several or more molecules exist in the target sequence, the amplification reaction proceeds. Accordingly, samples of the PCR method can be provided by a simple pretreatment of the bacteria with a lytic enzyme or a surfactant. For this reason, the method for detecting bacteria has merits higher than conventional methods.

The present invention provides gene sequences of a spacer region between a gene coding 16 S rRNA and a gene coding 23S rRNA in each *Pectinatus frisingensis* or *Pectinatus cerevisiiphilus*. By using a nucleotide sequence coding a 16S rRNA gene or oligonucleotide which is selected from the sequence as a primer for nucleic acid synthesis in the PCR method, and by gene amplification treatment, the present inventors have developed a quick and high sensitive method for judging the existence of *Pectinatus frisingensis* or *Pectinatus cerevisiiphilus* in samples.

The test samples may be beer or semi-products of beer, or a sample extracted from sewage and the like. The oligonucleotide for a primer may be a chemical synthetic or natural product.

DESCRIPTION OF THE PREFERRED EMBODIMENTS

As shown hereinafter, in the method of the present invention, *Pectinatus frisingensis* or *Pectinatus cerevisiiphilus* is detected by the PCR method. The base sequences used in the PCR method are, not by way of limitation, for example, above-mentioned (5), (6), (11) and (12). The primer length used in the PCR method is, not by way of limitation, 19–20 base length in above-mentioned (5), (6), (11) and (12), preferably, 10–50 base length.

When *Pectinatus frisingensis* is detected by the PCR method, the existence of the bacteria is judged by that the DNA fragments amplified in case of the combination of ① and ⑥ as the primer are about 700 base pairs and about 900 base pairs, and the DNA fragments amplified in case of the combination of ② and ⑥ as the primer are about 700 base pairs and about 900 base pairs. When these bands are detected by electrophoresis, it is judged that *Pectinatus frisingensis* present. Since the combination of the primers, in any cases, is specific for *Pectinatus frisingensis* bacteria, the genus can be detected. By parallel using two of the combination, further precise determination becomes possible. By changing the base sequences of the primers used in the PCR method, the length of the nucleotide sequences amplified can be changed.

On the other hand, when *Pectinatus cerevisiiphilus* is detected by the PCR method, the existence of the bacteria is judged by that the DNA fragments amplified in case of the combination of ③ and ⑦ are about 600 base pairs, the DNA fragments amplified in case of the combination of ④ and ⑦ are about 650 base pairs, and the DNA fragments amplified in case of the combination of ⑤ and ⑦ are about 700 base pairs. When these bands are detected by electrophoresis, it is judged that *Pectinatus cerevisiiphilus* is present. Since the combination of the primers, in any cases, is specific for *Pectinatus cerevisiiphilus* bacteria, the genus can be detected. By parallel using two or more of the combination, further precise determination becomes possible. By changing the base sequences of the primers used in the PCR method, the length of the nucleotide sequences amplified can be changed.

The temperature conditions of one cycle in the PCR method are 90–98° C. in a thermal denaturation reaction in which double-stranded DNA is changed to single-stranded DNA, 37–65° C. in an annealing reaction in which DNA is hybridized into primer template DNA, and 50–75° C. in a chain elongation reaction in which DNA polymerase is reacted. The target sequences can be amplified by several ten cycles. After PCR reaction, the reactant is separated by electrophoresis, and the nucleic acid is stained with ethidium bromide or the like. When the base length of the amplified nucleotide sequence is equal to the base length of the above target sequence, it can be judged that the bacteria to be detected are in the test sample. To detect the amplified nucleotide sequence, chromatography is usable.

The sequences of the present invention are described in the following:

SEQ ID NO: 1 The sequence length is 624, the sequence type is nucleic acid, the strandness is double, the topology is linear, the molecule type is genomic DNA, and the original source is *Pectinatus frisingensis* DSM6306.

SEQ ID NO: 2 The sequence length is 442, the sequence type is nucleic acid, the strandness is double, the topology is linear, the molecule type is genomic DNA, and the original source is *Pectinatus frisingensis* DSM6306.

SEQ ID NO: 3 The sequence length is 724, the sequence type is nucleic acid, the strandness is double, the topology is linear, the molecule type is genomic DNA, and the original source is *Pectinatus cerevisiiphilus* DSM20467.

SEQ ID NO: 4 The sequence length is 399, the sequence type is nucleic acid, the strandness is double, the topology is linear, the molecule type is genomic DNA, and the original source is *Pectinatus cerevisiiphilus* DSM20467.

SEQ ID NO: 5 The sequence length is 19, the sequence type is nucleic acid, the strandness is single, the topology is linear, the molecule type is genomic DNA, and the original source is *Pectinatus frisingensis* DSM6306.

SEQ ID NO: 6 The sequence length is 20, the sequence type is nucleic acid, the strandness is single, the topology is linear, the molecule type is genomic DNA, and the original source is *Pectinatus frisingensis* DSM6306.

SEQ ID NO: 7 The sequence length is 19, the sequence type is nucleic acid, the strandness is single, the topology is linear, the molecule type is genomic DNA, and the original source is *Pectinatus cerevisiiphilus* DSM20467.

SEQ ID NO: 8 The sequence length is 20, the sequence type is nucleic acid, the strandness is single, the topology is linear, the molecule type is genomic DNA, and the original source is *Pectinatus cerevisiiphilus* DSM20467.

SEQ ID NO: 9 The sequence length is 20, the sequence type is nucleic acid, the strandness is single, the topology is linear, the molecule type is genomic DNA, and the original source is *Pectinatus cerevisiiphilus* DSM20467.

SEQ ID NO: 10 The sequence length is 20, the sequence type is nucleic acid, the strandness is single, the topology is linear, the molecule type is genomic DNA, and the original source is *Pectinatus frisingensis* DSM6306.

SEQ ID NO: 11 The sequence length is 20, the sequence type is nucleic acid, the strandness is single, the topology is linear, the molecule type is genomic DNA, and the original source is *Pectinatus cerevisiiphilus* DSM20467.

The present invention is described by working examples in the following. The present invention is not limited by these examples.

EXAMPLE 1

Preparation of Test Samples

*Pectinatus frisingensis* DSM6306 and *Pectinatus cerevisiiphilus* DSM20467 were used as bacterial strains belonging to *Pectinatus*. To confirm the specificity of *Pectinatus frisingensis* and *Pectinatus cerevisiiphilus* primers shown in SEQ ID NO: 5, 6, 7, 8, 9, 10 and 11 in the present invention, the other bacteria shown in Table 1 were used. These bacteria were cultivated on suitable culture mediums, and the strains were collected by centrifugation. The DNA from the strains were extracted in accordance with the description of SHIN-SEIKAGAKU-JIKKEN-KOZA 2, Nucleic acid I, Separation and Purification, p.p. 20–21 (edited by Japan Biochemical Learned Society, Tokyo-Kagaku-Dojin), and a DNA solution was obtained.

TABLE 1

| Bacteria No. | Bacteria type | Strain Name | Remarks |
| --- | --- | --- | --- |
| 1 | *Pectinatus frisingensis* | DSM63O6 | Type strain |
| 2 | *Pectinatus cerevisiiphilus* | DSM20467 | Type strain |
| 3 | *Selenomonas lacticifex* | DSM20757 | Type strain |
| 4 | *Zymophilus raffinosivorans* | DSM20765 | Type strain |
| 5 | *Zymophilus paucivorans* | DSM20756 | K-12 |
| 6 | *Escherichia coli* | IF03301 | Type strain |
| 7 | *Megasphaera cerevisiae* | DSM20462 | Type strain |
| 8 | *Lactobacillus acidophilus* | IF013951 | Type strain |
| 9 | *Lactobacillus plantarum* | JCM1149 | Type strain |
| 10 | *Lactobacillus brevis* | JCM1059 | Type strain |
| 11 | *Lactococcus lactis* | JCM5805 | Type strain |
| 12 | *Leuconostoc mesenteroides* | JCM6124 | Type strain |
| 13 | *Pediococcus damnosus* | JCM5886 | Type strain |

EXAMPLE 2

Cloning of Spacer Regions between the Gene Coding 16S rRNA and the Gene Coding 23S rRNA of *Pectinatus frisingensis*, and Determination of the Base Sequences (1) Selection and Synthesis of Oligonucleotide Primers for Amplification of 16S/23S rRNA Spacer Region by the PCR Method Since the base sequences of the 16S ribosomal RNA gene of *Pectinatus frisingensis* were apparent (International Journal of Systematic Bacteriology, Vol. 40, p.p. 19–27 (1990)), the primers were selected on the basis of the 557–576$^{th}$ base sequences.

Since the base sequences of the 23S ribosomal RNA gene of *Pectinatus frisingensis* were apparent (Systematic Applied Microbiology, Vol. 15, p.p. 487–501 (1990), EMBL Accession Number X48423), the primers were selected on the basis of the 1–20$^{th}$ base sequences to obtain corresponding comprehensive sequences. The synthesis was entrusted to Sawady Technology Co., Ltd.

(2) Amplification of 16S/23S rRNA Spacer Regions by the PCR Method

The *Pectinatus frisingensis* DNA solution 0.1 μg, which was prepared in Example 1, was placed in a 0.2 ml tube (manufactured by Perkin-Elmer), 5 μl of 10× buffer in a rTaq DNA Polymerase Kit (Toyobo Co., Ltd.), 3 μl of 25 mM $MgCl_2$, 5 μl of a 2 mM dNTP mixture solution (dATP, dGTP, dCTP and dTTP), 0.5 μl of 5 units/μl of rTaq polymerase, and each 0.5 μl of 100 mM primers prepared in Example 2-(1) were added to the solution, and then sterilized distilled water was added to obtain final volume of 50 μl. The tube was set on a thermal cycler of an automatic gene amplification device (Perkin Elmer) and the amplification method was conducted. The reaction was repeated by 30 cycles, and one cycle had the following conditions:

Denaturation at 94° C. for 2.5 minutes; Denaturation at 94° C. for 30 seconds; Annealing of primers at 55° C. for 30 seconds; and synthetic reaction at 72° C. for 30 seconds. After the reaction, using 5 µl of the solution, electrophoresis was conducted by agarose gel. DNA was dyed with ethidium bromide, and amplified DNA was observed. The result shows that about 1600 bp (abbreviated as "long" hereinafter) DNA and about 1400 bp (abbreviated as "short" hereinafter) DNA were amplified.

(3) Cloning and Sequencing of the Spacer Region "Long"

Using a high pure PCR product purification kit (Baringer Manhaim), unreactive dNTPs was removed from the solution after the PCR reaction. To the resulting amplified DNA 100 ng, 2 µl of plasmid pCR 2.1 contained in a TA cloning kit (INVITROGEN), 1 µl of ligase and 1 µl of buffer were added, and then sterilized water was added to obtain the total volume of 10 µl. After the solution was reacted at 14° C. for 4 hours, 2 µl of the solution and 2 µl of 0.5 M, β-mercaptoethanol were added to *Escherichia coli* INVα' F competent cells, and placed in ice for 30 minutes. Then, the solution was heated at 42° C. for 30 seconds, and plasmid transformation to the bacteria was conducted. To the transformed bacteria, 250 µl of a SOC culture (2.0% Tryptone, 0.5% yeast extract, 10.0 mM NaCl, 2.5 mM KCl, 10.0 mM $MgCl_2$-$6H_2O$, and 20.0 mM glucose) was added, and the mixture was shaken at 37° C. for 60 minutes, then transferred to a LB plate culture medium containing 50 µg/ml of ampicillin and 40 µg/ml X-Gal, and cultured at 37° C. overnight. The expressed white colony was transferred to 3 ml of a LB liquid culture medium containing 50 µg/ml of ampicillin, and cultured at 37° C. overnight.

After the cultivation, plasmids were extracted from the bacteria with a plasmid mini kit QIAGEN). A part of the resulting plasmids was taken out and reacted with a restriction enzyme EcoRI (manufactured by Takara Shuzo) at 37° C. for 60 minutes, and separated by agarose electrophoresis. The DNA was dyed with ethidium bromide, and insertion of "long" was confirmed. 500 ng of the residual plasmid was reacted with restriction enzyme SmaI (manufactured by TOYOBO Co., Ltd.) at 30° C. for 60 minutes. To the reactant, 2 µl of 3 M sodium acetate and 500 µl of 100% ethanol were added, and the mixture was placed in ice for 15 minutes and centrifuged at 15000 rpm for 15 minutes, and the supernatant was removed. To the precipitate, 500 µl of 70% ethanol was added, the mixture was centrifuged at 15000 rpm for 15 minutes, and the supernatant was removed, and dried for 10 minutes under reduced pressure. Sterilized water was added to dissolve the precipitate, and the mixture was reacted with restriction enzyme XbaI (Baringer Manhaim) at 37° C. for 60 minutes. To the reactant, equivalent phenol/chloroform (equivalent mixture liquid) was added and gently mixed, the mixture was centrifuged at 15000 rpm for 15 minutes, and the water layer (upper layer) was recovered.

To the recovery liquid, equivalent water-saturated ether was added and gently mixed, and the mixture was centrifuged at 15000 rpm for 15 minutes to remove the ether layer (upper layer). To the remaining water layer, 2 µl of 3M sodium acetate and 500 µl of 100% ethanol were added, and the mixture was placed in ice for 15 minutes and centrifuged at 15000 rpm for 15 minutes to remove the supernatant. To the precipitate, 500 µl of 70% ethanol was added, and the mixture was centrifuged at 15000 rpm for 15 minutes to remove the supernatant, and the residue was dried under reduced pressure for 10 minutes, and 20 µl of sterilized distillation water was added. To 5 µl of the solution, 1 µl of 10× buffer contained in a blunting kit (Takara Shuzo Co., Ltd.) and 3 µl of sterilized distillation water were added, and the mixture was maintained at 70° C. for 5 minutes, 1 µl of T4 DNA polymerase was added, and the mixture was maintained at 37° C. for 5 minutes to obtain blunt ends. After T4 DNA polymerase was inactivated by stirring, 40 µl of ligation solution A and 10 µl of ligation solution B were added, and the mixture was maintained at 16° C. for 30 minutes to conduct internal ligation.

The reactant 2 µl and 2 µl of 0.5M β-mercaptoethanol were added to a *Escherichia coli* INVα' F competent cell, and the mixture was placed in ice for 30 minutes and heated at 42° C. for 30 seconds, and the plasmid was transformed to the *Escherichia coli*. To the transformed *Escherichia coli*, a SOC culture medium (2.0% Tryptone, 0.5% Yeast extract, 10.0 mM NaCl, 2.5 mM KCl, 10.0 mM $MgCl_2$-$6H_2O$, 20.0 mM glucose) 250 µl was added, and the mixture was shaken at 37° C. for 60 minutes and spread on a LB plate culture medium containing 50 µg/ml ampicillin to culture at 37° C. overnight. Appeared white colonies were inoculated into 3 ml of a LB liquid culture medium containing 50 µg/ml of ampicillin and cultured at 37° C. overnight. After the culture, the plasmid was extracted from the *Escherichia coli* with a plasmid mini kit (QIAGEN Company).

Using such obtained plasmid as a template, a sequence reaction was conducted. As the sequencing primers, an IRD41 Infrared Dye Labeled M13 Forward primer and an IRD41 Infrared Dye Labeled M13 Reverse primer (manufactured by Nisshinbo, sold by Aroka Co., Ltd.) were used. As the reaction liquid, SequiTherm (trademark) Long-Read (trademark) Cycle Sequencing Kit-LC (manufactured by EPICENTRE TECHNOLOGIES) was used. 4000L Long ReadIR (trademark) DNA Sequencing System (manufactured by LI-COR) was used for the determination of the base sequences.

The gene sequence of spacer region "long" between the gene coding 16S rRNA and the gene coding 23S rRNA of *Pectinatus frisingensis* DSM6306 bacteria is shown in SEQ ID NO: 1.

(4) Cloning and Sequencing of Spacer Region "Short"

Using a high pure PCR product purification kit (Baringer Manhaim), unreactive dNTPs was removed from the solution after the PCR reaction in Example 2-(2). To the resulting amplified DNA 100 ng, 2 µl of plasmid pCR 2.1 contained in a TA cloning kit (INVITROGEN), 1 µl of ligase and I µl of buffer were added, and then sterilized water was added to obtain the total volume of 10 µl. After the solution was reacted at 14° C. for 4 hours, 2 µl of the solution and 2 µl of 0.5 M-mercaptoethanol were added to *Escherichia coli* INVα' F competent cells, and placed in ice for 30 minutes. Then, the solution was heated at 42° C. for 30 seconds, and plasmid transformation to the bacteria was conducted. To the transformed bacteria, 250 µl of a SOC culture (2.0% Tryptone, 0.5% yeast extract, 10.0 mM NaCl, 2.5 mM KCl, 10.0 mM $MgCl_2$-$6H_2O$, and 20.0 mM glucose) was added, and the mixture was shaken at 37° C. for 60 minutes, then transferred to a LB plate culture medium containing 50 µl/ml of ampicillin and 40 µg/ml X-Gal, and cultured at 37° C. overnight. The appeared white colony was transferred to 3 ml of a LB liquid culture medium containing 50 µg/ml of ampicillin, and cultured at 37° C. overnight. After the cultivation, plasmid was extracted from the bacteria with a plasmid mini kit QIAGEN).

A part of the resulting plasmid was taken out and reacted with a restriction enzyme EcoRI (manufactured by Takara Shuzo) at 37° C. for 60 minutes, and separated by agarose electrophoresis. The DNA was dyed with ethidium bromide, and insertion of "short" was confirmed. 500 ng of the residual plasmid was reacted with restriction enzyme SmaI (manufactured by TOYOBO Co., Ltd.) at 30° C. for 60 minutes. To the reactant, 2 μl of 3 M sodium acetate and 500 μl of 100% ethanol were added, and the mixture was placed in ice for 15 minutes and centrifuged at 15000 rpm for 15 minutes, and the supernatant was removed. To the precipitate, 500 μl of 70% ethanol was added, the mixture was centrifuged at 15000 rpm for 15 minutes, and the supernatant was removed, and dried for 10 minutes under reduced pressure. Sterilized water was added to dissolve the precipitate, and the mixture was reacted with restriction enzyme XbaI (Baringer Manhaim) at 37° C. for 60 minutes. To the reactant, equivalent phenol/chloroform (equivalent mixture liquid) was added and gently mixed, the mixture was centrifuged at 15000 rpm for 15 minutes, and the water layer (upper layer) was recovered. To the recovery liquid, equivalent water-saturated ether was added and gently mixed, and the mixture was centrifuged at 15000 rpm for 15 minutes to remove the ether layer (upper layer).

To the remaining water layer, 2 μl of 3M sodium acetate and 500 μl of 100% ethanol were added, and the mixture was placed in ice for 15 minutes and centrifuged at 15000 rpm for 15 minutes to remove the supernatant. To the precipitate, 500 μl of 70% ethanol was added, and the mixture was centrifuged at 15000 rpm for 15 minutes to remove the supernatant, and the residue was dried under reduced pressure for 10 minutes, and 20 μl of sterilized distilled water was added. To 5 μl of the solution, 1 μl of 10× buffer contained in a blunting kit (Takara Shuzo Co., Ltd.) and 3 μl of sterilized distilled water were added, and the mixture was maintained at 70° C. for 5 minutes, 1 μl of T4 DNA polymerase was added, and the mixture was maintained at 37° C. for 5 minutes to obtain blunt ends. After T4 DNA polymerase was inactivated by stirring, 40 μl of ligation solution A and 10 μl of ligation solution B were added, and the mixture was maintained at 16° C. for 30 minutes to conduct internal ligation. 2 μl of the reactant and 2 μl of 0.5M β-mercaptoethanol were added to a Escherichia coli INVα' F competent cell, and the mixture was placed in ice for 30 minutes and heated at 42° C. for 30 seconds, and the plasmid was transformed to the Escherichia coli.

To the transformed Escherichia coli, 250 μl of SOC culture medium (2.0% Tryptone, 0.5% Yeast extract, 10.0 mM NaCl, 2.5 mM KCl, 10.0 mM $MgCl_2$-$6H_2O$, 20.0 mM glucose) was added, and the mixture was shaken at 37° C. for 60 minutes and spread on a LB plate culture medium containing 50 μg/ml ampicillin to culture at 37° C. overnight. Appeared white colonies were inoculated into 3 ml of a LB liquid culture medium containing 50 μg/ml of ampicillin and cultured at 37° C. overnight. After the culture, the Plasmid was extracted from the Escherichia coli with a plasmid mini kit (QIAGEN Company).

Using such obtained plasmid as a template, a sequence reaction was conducted. As the sequencing primers, an IRD41 Infrared Dye Labeled M13 Forward primer and an IRD41 Infrared Dye Labeled M13 Reverse primer (manufactured by Nisshinbo, sold by Arok co., Ltd.) were used. As the reaction liquid, SequiTherma (trademark) Long-Read (trademark) Cycle Sequencing Kit-LC (manufactured by EPICENTRE TECHNOLOGIES) was used. 4000L Long ReadIR (trademark) DNA Sequencing System (manufactured by LI-COR) was used for the determination of the base sequences.

The gene sequence of spacer region "short" between the gene coding 16S rRNA and the gene coding 23S rRNA of Pectinatus frisingensis is shown in SEQ ID NO: 2.

EXAMPLE 3

Detection of *Pectinatus frisingensis* by the PCR Method (1) Selection and Synthesis of a Primer for *Pectinatus frisingensis*

The sequences specific for *Pectinatus frisingensis* by using DNASIS (tradename of Hitachi Soft Engineering Ltd., Co.) on the basis of SEQ ID NO: 1 and SEQ ID NO: 2 were analyzed. The result selected a sequence of $377^{th}$ to $395^{th}$ on the gene sequence of the spacer region between the gene coding 16S rRNA and the gene coding 23S rRNA of *Pectinatus frisingensis* of SEQ ID NO: 1, and a sequence of $195^{th}$ to $213^{th}$ on the gene sequence of the spacer region between the gene coding 16S rRNA and the gene coding 23S rRNA of *Pectinatus frisingensis* of SEQ ID NO: 2. (SEQ ID NO: 5.)

In addition, the similar analysis selected a sequence of $361^{st}$ to $380^{th}$ on the gene sequence of the spacer region between the gene coding 16S rRNA and the gene coding 23S rRNA of *Pectinatus frisingensis* of SEQ ID NO: 1, and a sequence of $179^{th}$ to $198^{th}$ on the gene sequence of the spacer region between the gene coding 16S rRNA and the gene coding 23S rRNA of *Pectinatus frisingensis* of SEQ ID NO: 2. (SEQ ID NO: 6.)

Further, specific primer showing in SEQ ID NO: 10 was selected by a gone sequence coding 16S rRNA of *Pectinatus frisingensis*. The oligonucleotides were chemically synthesized by the same method as in Example (2) Detection and identification of *Pectinatus frisingensis* by the primers having the sequences of SEQ ID NO: 6 and SEQ ID NO: 10.

The DNA solutions of bacteria prepared in Example 1 were treated with the primers synthesized in Example 3 (SEQ ID NO:6 and SEQ ID NO: 10) by PCR. The temperature conditions of the PCR were as follows:

Thermal denaturation; 94° C., 30 seconds
Annealing; 55° C., 30 seconds
Chain elongation reaction; 72° C., 30 seconds One cycle of the conditions was repeated 35 times. After the PCR, the reactant was electrophoresed with agalose gel at constant 100 V for 30 minutes. A pHY marker was also electrophoresed at the same time as a molecular weight marker. After the electrophoresis, the agarose gel was stained in about 0.5 μg/ml of an ethidium bromide solution for 20 minutes, and ultraviolet was applied to observe the gel and take a photograph of the gel. By the observation or the photography of the gel, the base length of the amplified products was determined from the relative migration distance of the molecular marker.

As shown in FIG. 1, bands of about 700 bps and about 900 bps were detected only in case of *Pectinatus frisingensis*.

From the results, when the oligonucleotides of SEQ ID NO: 6 and SEQ ID NO: 10 were used as PCR primers, the bands having objective length were detected only in case of *Pectinatus frisingensis*. Accordingly, it was shown that each oligonucleotide of the present invention correctly recognized the gene sequences of the spacer region between the gene coding 16S rRNA and the gene coding 23S rRNA of *Pectinatus frisingensis*, and the base sequence targeted on the gene coding 16S rRNA. Moreover, the bands having the aimed length were not observed in the same genus *Pectinatus cerevisiiphilus*, and relative strictly anaerobic bacteria and Gram-positive bacteria. Accordingly, *Pectinatus frisingensis* can be specifically detected, and at the same time also determined by the present invention.

EXAMPLE 4

Cloning and Determination of the Base Sequence of the Spacer Regions between the Gene Coding 16S rRNA and the Gene Coding 23S rRNA of *Pectinatus cerevisiiphilus*

(1) Selection and Synthesis of Oligonucleotide Primers for Amplifying 16S/23S rRNA Spacer Regions by PCR As the base sequence of 16S ribosome RNA gene of *Pectinatus cerevisiiphilus* is disclosed in International Journal of Systematic Bacteriology, Vol. 40, pages 19–27 (1990), the primers were selected on the basis of the base 1 h sequence of $557^{th}$–$576^{th}$.

The base sequence of 23 ribosome RNA gene of *Pectinatus cerevisiiphilus* had not been disclosed, but the base sequence of 23 ribosome RNA gene of *Pectinatus frisingensis* had been disclosed in Systematic Applied Microbiology, Vol. 15, pages 487–501 (1990), EMBL Accession Number X48423. The primer was selected to obtain the complementary sequence corresponding to the base sequence of $1^{st}$–$20^{th}$ of 23 ribosome RNA gene of *Pectinatus frisingensis*. Sawaday Technology was entrusted with the synthesis.

(2) Amplification of 16S/23S rRNA by PCR

The DNA solution 0.1 µg of *Pectinatus cerevisiiphilus* prepared in Example 1 was charged in a 0.2 ml tube (Perkin-Elmer Co.), 5 µl of 10× buffer in rTaq DNA Polymerase Kit (TOYOBO Co., Ltd.), 3 µl of 25 mM $MgCl_2$, 5 µl of 2 mM dNTP mixture solution (dATP, dGTP, dCTP and dTTP), 0.5 µl of 5 unit/µl rTaq-polymerase, each 0.5 µl of the 100 mM primers prepared in Example 2-(1) were added, and sterilized water was added to obtain final volume of 50 µl. The tube was set in a thermal cycler of an automatic gene amplification device (Perkin-Elmer Co.) and amplification reaction was conducted. 30 cycles were carried under the reaction conditions of one cycle of denaturation at 94T for 2.5 minutes, denaturation at 94° C. for 30 seconds, primer annealing at 55° C. for 30 seconds and synthetic reaction at 72° C. for 30 seconds. After the reaction, 5 µl of the reactant was used in agarose gel electrophoresis, the DNA was stained with ethidium bromide, and the amplified DNA was observed. As a result, DNA of about 1700 bp (abbreviated as "long") and DNA of about 1400 bp (abbreviated as "short") were amplified.

(3) Cloning and Sequencing of the Spacer Region "Long"

Using a high pure PCR product purification kit (Baringer Manhaim), unreactive dNTPs was removed from the solution after the PCR reaction. To 10 ng of the resulting amplified DNA, 2 µl of plasmid pCR 2.1 contained in a TA cloning kit (INVITROGEN), 1 µl of ligase and 1 µl of buffer were added, and then sterilized water was added to obtain the total volume of 10 µl. After the solution was reacted at 14° C. for 4 hours, 2 µl of the solution and 2 µl of 0.5 M, β-mercaptoethanol were added to *Escherichia coli* INVα' F competent cells, and placed in ice for 30 minutes. Then, the solution was heated at 42° C. for 30 seconds, and plasmid transformation to the bacteria was conducted. To the transformed bacteria, 250 µl of a SOC culture (2.0% Tryptone, 0.5% yeast extract, 10.0 mM NaCl, 2.5 mM KCl, 10.0 mM $MgCl_2$-$6H_2O$, and 20.0 mM glucose) was added, and the mixture was shaken at 37° C. for 60 minutes, then transferred to a LB plate culture medium containing 50 µg/ml of ampicillin and 40 µg/ml X-Gal, and cultured at 37° C. overnight. The expressed white colony was transferred to 3 ml of a LB liquid culture medium containing 50 µg/ml of ampicillin, and cultured at 37° C. overnight.

After the cultivation, plasmids were extracted from the bacteria with a plasmid mini kit (QIAGEN). A part of the resulting plasmids was taken out and reacted with a restriction enzyme EcoRI (manufactured by Takara Shuzo) at 37° C. for 60 minutes, and separated by agarose electrophoresis. The DNA was dyed with ethidium bromide, and insertion of "long" was confirmed. 500 ng of the residual plasmid was reacted with restriction enzyme SmaI (manufactured by TOYOBO Co., Ltd.) at 30° C. for 60 minutes. To the reactant, 2 µl of 3 M sodium acetate and 500 µl of 100% ethanol were added, and the mixture was placed in ice for 15 minutes and centrifuged at 15000 rpm for 15 minutes, and the supernatant was removed. To the precipitate, 500 µl of 70% ethanol was added, the mixture was centrifuged at 15000 rpm for 15 minutes, and the supernatant was removed, and the residual was dried for 10 minutes under reduced pressure. Sterilized water was added to dissolve the precipitate, and the mixture was reacted with restriction enzyme XbaI (Baringer Manhaim) at 37° C. for 60 minutes. To the reactant, equivalent phenol/chloroform (equivalent mixture liquid) was added and gently mixed, the mixture was centrifuged at 15000 rpm for 15 minutes, and the water layer (upper layer) was recovered. To the recovery liquid, equivalent water-saturated ether was added and gently mixed, and the mixture was centrifuged at 15000 rpm for 15 minutes to remove the ether layer (upper layer). To the remaining water layer, 2 µl of 3M sodium acetate and 500 µl of 100% ethanol were added, and the mixture was placed in ice for 15 minutes and centrifuged at 15000rpm for 15 minutes to remove the supernatant.

To the precipitate, 500 µl of 70% ethanol was added, and the mixture was centrifuged at 15000 rpm for 15 minutes to remove the supernatant, and the residue was dried under reduced pressure for 10 minutes, and 20 µl of sterilized distillation water was added. To 5 µl of the solution, 1 µl of 10× buffer contained in a blunting kit (Takara Shuzo Co., Ltd.) and 3 µl of sterilized distillation water were added, and the mixture was maintained at 70° C. for 5 minutes, 1 µl of T4 DNA polymerase was added, and the mixture was maintained at 37° C. for 5 minutes to obtain blunt ends. After T4 DNA polymerase was inactivated by stirring, 40 µl of ligation solution A and 10 µl of ligation solution B were added, and the mixture was maintained at 16° C. for 30 minutes to conduct internal ligation. 2 µl of the reactant and 2 µl of 0.5M β-mercaptoethanol were added to *Escherichia coli* INVα' F competent cells, and the mixture was placed in ice for 30 minutes and heated at 42° C. for 30 seconds, and the plasmid was transformed to the *Escherichia coli*.

To the transformed *Escherichia coli*, 250 µl of a SOC culture medium (2.0% Tryptone, 0.5% Yeast extract, 10.0 mM NaCl, 2.5 mM KCl, 10.0 mM $MgCl_2$-$6H_2O$, 20.0 mM glucose) was added, and the mixture was shaken at 37° C. for 60 minutes and spread on a LB plate culture medium containing 50 µg/ml of ampicillin to culture at 37° C. overnight. Appeared white colonies were-inoculated into 3 ml of a LB liquid culture medium containing 50 µg/ml of ampicillin and cultured at 37° C. overnight. After the culture, the plasmid was extracted from the *Escherichia coli* with a plasmid mini kit (QIAGEN Company).

Using such obtained plasmid as a template, a sequence reaction was conducted. As the sequencing primers, an IDRD41 Infrared Dye Labeled M13 Forward primer and an IRD41 Infrared Dye Labeled M13 Reverse primer (manufactured by Nisshinbo, sold by Aroka Co., Ltd.) were used. As the reaction liquid, SequiTherm (trademark) Long-Read (trademark) Cycle Sequencing Kit-LC (manufactured by EPICENTRE TECHNOLOGIES) was used. 4000L Long ReadIR (trademark) DNA Sequencing System (manufactured by LI-COR) was used for the determination of the base sequences.

The gene sequence of spacer region "long" between the gene coding 16S rRNA and the gene coding 23S rRNA of *Pectinatus cerevisiiphilus* is shown in SEQ ID NO: 3.

(4) Cloning and Sequencing of Spacer Region "Short"

Using a high pure PCR product purification kit (Baringer Manhaim), unreactive dNTPs was removed from the solution after the PCR reaction in Example 4-(2). To 100 ng of the resulting amplified DNA, 2 μl of plasmid pCR 2.1 contained in a TA cloning kit (INVITROGEN), 1 μl of ligase and 1 μl of buffer were added, and then sterilized water was added to obtain the total volume of 10 μl. After the solution was reacted at 14° C. for 4 hours, 2 μl of the solution and 2 μl of 0.5 M β-mercaptoethanol were added to *Escherichia coli* INVα' F competent cells, and placed in ice for 30 minutes. Then, the solution was heated at 42° C. for 30 seconds, and plasmid transformation to the bacteria was conducted. To the transformed bacteria, 250 μl of a SOC culture (2.0% Tryptone, 0.5% yeast extract, 10.0 mM NaCl, 2.5 mM KCl, 10.0 mM $MgCl_2$-$6H_2O$, and 20.0 mM glucose) was added, and the mixture was shaked at 37° C. for 60 minutes, then transferred to a LB plate culture medium containing 50 μg/ml of ampicillin and 40 μg/ml X-Gal, and cultured at 37° C. overnight. The appeared white colony was transferred to 3 ml of a LB liquid culture medium containing 50 μg/ml of ampicillin, and cultured at 37° C. overnight. After the cultivation, plasmid was extracted from the bacteria with a plasmid mini kit (QIAGEN).

Apart of the resulting plasmid was taken out and reacted with a restriction enzyme EcoRI (manufactured by Takara Shuzo) at 37° C. for 60 minutes, and the reactant was separated by agarose electrophoresis. The DNA as dyed with ethidium bromide, and insertion of "short" was confirmed. 500 ng of the residual plasmid was reacted with restriction enzyme SmaI (manufactured by TOYOBO Co., Ltd.) at 30° C. for 60 minutes. To the reactant, 2 μl of 3 M sodium acetate and 500 μl of 100% ethanol were added, and the mixture was placed in ice for 15 minutes and centrifuged at 15000 rpm for 15 minutes, and the supernatant was removed. To the precipitate, 500 μl of 70% ethanol was added, the mixture was centrifuged at 15000 rpm for 15 minutes, and the supernatant was removed, and the residue was dried for 10 minutes under reduced pressure. Sterilized water was added to dissolve the precipitate, and the mixture was reacted with restriction enzyme BamHI (Takara Shuzo Co.) at 37° C. for 60 minutes. To the reactant, equivalent phenol/chloroform (equivalent mixture liquid) was added and gently mixed, the mixture was centrifuged at 15000 rpm for 15 minutes, and the water layer (upper layer) was recovered. To the recovery liquid, equivalent water-saturated ether was added and gently mixed, and the mixture was centrifuged at 15000 rpm for 15 minutes to remove the ether layer (upper layer). To the remaining water layer, 2 μl of 3M sodium acetate and 500 μl of 100% ethanol were added, and the mixture was placed in ice for 15 minutes and centrifuged at 15000 rpm for 15 minutes to remove the supernatant.

To the precipitate, 500 μl of 70% ethanol was added, and the mixture was centrifuged at 15000 rpm for 15 minutes to remove the supernatant, and the residue was dried under reduced pressure for 10 minutes, and 20 μl of sterilized distilled water was added. To 5 μl of the solution, 1 μl of 10× buffer contained in a blunting kit (Takara Shuzo Co., Ltd.) and 3 μl of sterilized distilled water were added, and the mixture was maintained at 70° C. for 5 minutes, 1 μl of T4 DNA polymerase was added, and the mixture was maintained at 37° C. for 5 minutes to obtain blunt ends. After T4 DNA polymerase was inactivated by stirring, 40 μl of ligation solution A and 10 μl of ligation solution B were added, and the mixture was maintained at 16° C. for 30 minutes to conduct internal ligation. 2 μl of the reactant and 2 μl of 0.5M β-mercaptoethanol were added to a *Escherichia coli* INVα' F competent cell, and the mixture was placed in ice for 30 minutes and heated at 42° C. for 30 seconds, and the plasmid was transformed to the *Escherichia coli*. To the transformed *Escherichia coli* 250 μl of a SOC culture medium (2.0% Tryptone, 0.5% Yeast extract, 10.0 mM NaCl, 2.5 mM KCl, 10.0 mM $MgCl_2$$6H_2O$, 20.0 mM glucose) was added, and the mixture was shaken at 37° C. for 60 minutes and spread on a LB plate culture medium containing 50 μg/ml ampicillin to culture at 37° C. overnight. Appeared white colonies were inoculated into 3 ml of a LB liquid culture medium containing 50 μg/ml of ampicillin and cultured at 37° C. overnight. After the culture, the plasmid was extracted from the *Escherichia coli* with a plasmid kit (QIAGEN Company).

Using such obtained plasmid as a template, a sequence reaction was conducted. As the sequencing primers, an IRD41 Infrared Dye Labeled M13 Forward primer and an IRD41 Infrared Dye Labeled M13 Reverse primer (manufactured by Nisshinbo, sold by Aroka Co., Ltd.) were used. As the reaction liquid, SequiTherm (trademark) Long-Read (trademark) Cycle Sequencing Kit-LC (manufactured by EPICENTRE TECHNOLOGIES) was used. 4000L Long ReadIR (trademark) DNA Sequencing System (manufactured by LI-COR) was used for the determination of the base sequences.

The gene sequence of spacer region "short" between the gene coding 16S rRNA and the gene coding 23S rRNA of *Pectinatus cerevisiiphilus* is shown in SEQ ID NO: 4.

EXAMPLE 5

Detection of *Pectinatus cerevisiiphilus* by the PCR Method (1) Selection and Synthesis of a Primer for *Pectinatus cerevisiiphilus*

The sequences specific for *Pectinatus cerevisiiphilus* using DNASIS (tradename of Hitachi Soft Engineering Ltd., Co.) on the basis of SEQ ID NO: 3 were analyzed. The result selected a sequence of $135^{th}$ to $153^{rd}$ on the gene sequence of the spacer region between the gene coding 16S rRNA and the gene coding 23S rRNA of *Pectinatus cerevisiiphilus* of SEQ ID NO: 3. (SEQ ID NO: 7.)

In addition, the similar analysis selected a sequence of $172^{nd}$ to $191^{st}$ on the gene sequence of the spacer region between the gene coding 16S rRNA and the gene coding 23S rRNA of *Pectinatus cerevisiiphilus* of SEQ ID NO: 3. (SEQ ID NO: 8.)

The similar analysis also selected a sequence of $203^{rd}$ to $222^{nd}$ on the gene sequence of the spacer region between the gene coding 16S rRNA and the gene coding 23S rRNA of *Pectinatus cerevisiiphilus* of SEQ ID NO: 3. (SEQ ID NO: 9.)

Further, specific primer showing in SEQ ID NO: 11 was selected by a gene sequence coding 16S rRNA of *Pectinatus cerevisiiphilus*. The oligonucleotides were chemically synthesized by the same method as in Example 2-(1).

(2) Detection and Identification of *Pectinatus cerevisiiphilus* by the Primers Having the Sequences of SEQ ID NO: 7 and SEQ ID NO: 11.

The DNA solutions of bacteria prepared in Example 1 were treated with the primers synthesized in Example 5-(1) (SEQ ID NO: 7 and SEQ ID NO: 11) by PCR. The temperature conditions of the PCR were as follows:

Thermal denaturation; 94° C., 30 seconds
Annealing; 55° C., 30 seconds
Chain elongation reaction; 72° C., 30 seconds One cycle of the conditions was repeated 35 times. After the PCR, the reactant was electrophoresed with agalose gel at constant 100 V for 30 minutes. A pHY marker was also electrophoresed at the same time as a molecular weight marker. After the electrophoresis, the gel was stained with 5 μg/ml of an ethidium bromide solution for 20 minutes, and ultraviolet was applied to observe the gel and take a photograph of the gel. By the observation or the photography of the gel, the base length of the amplified products was determined from the relative migration distance with a molecular weight marker.

Figure 2:
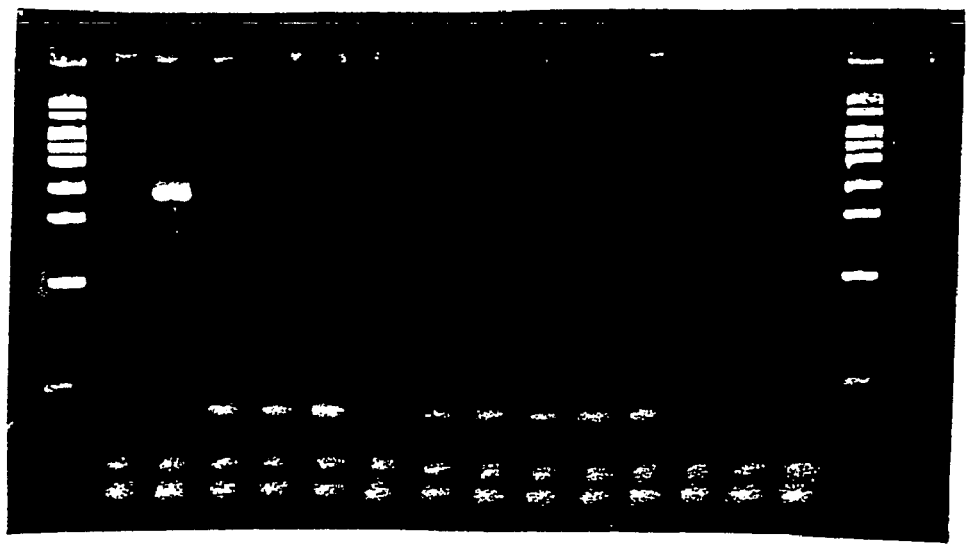
FIG. 2. It shows Electrophoretogram in Example 5.

As shown in FIG. 2, a band of about 600 bps was detected only in case of *Pectinatus cerevisiiphilus*.

From the results, when the oligonucleotides of SEQ ID NO: 7 and SEQ ID NO: 11 were used as PCR primers, the band having objective length was detected only in case of *Pectinatus cerevisiiphilus*. Accordingly, it was shown that each oligonucleotide of the present invention correctly recognized the gene sequences of the spacer region between the gene coding 16S rRNA and the gene coding 23S rRNA of *Pectinatus cerevisiiphilus*, and the base sequence targeted on the gene coding 16S rRNA. Moreover, the bands having the aimed length were not observed in the same genus *Pectinatus frisingensis*, and relative strictly anaerobic bacteria and Gram-positive bacteria. Accordingly, *Pectinatus cerevisiiphilus* can be specifically detected, and at the same time also determined by the present invention.

By the present invention, the genes of the spacer region constituted between the 16S rRNA genes and the 23S rRNA genes of *Pectinatus frisingensis* and *Pectinatus cerevisiiphilus* have been proved, and a method for quickly and reliably detecting *Pectinatus frisingensis* and *Pectinatus cerevisiiphilus* can be provided by using a part or all of the gene sequences.

What is claimed is:

1. An isolated nucleic acid comprising SEQ ID NO: 1.
2. An isolated nucleic acid comprising SEQ ID NO: 2.
3. An isolated nucleic acid comprising SEQ ID NO: 5 or SEQ ID NO: 6.
4. A method for detecting *Pectinatus frisingensis* comprising carrying out a gene amplification assay wherein a nucleic acid comprising instant SEQ ID NO: 1 is produced, and detecting the presence of the amplification product, wherein the presence of SEQ ID NO: 1 is indicative of the presence of *Pectinatus frisingensis*.
5. A method for detecting *Pectinatus frisingensis* comprising carrying out a gene amplification assay wherein a nucleic acid comprising instant SEQ ID NO: 2 is produced, and detecting the presence of the amplification product, wherein the presence of SEQ ID NO: 2 is indicative of the presence of *Pectinatus frisingensis*.
6. A method for detecting *Pectinatus frisingensis* comprising carrying out a gene amplification assay wherein SEQ ID NO: 5 or SEQ ID NO: 6 is used as a primer in conjunction with a primer sequence which hybridizes to the *Pectinatus frisingensis* 16S rRNA gene, and detecting the presence of an amplification product, wherein the presence of an amplification product is indicative of the presence of *Pectinatus frisingensis*.
7. A method according to claim 6 wherein the primer sequence which hybridizes to the *Pectinatus frisingensis* 16S rRNA gene is SEQ ID NO: 10.

* * * * *

SEQUENCE LISTING

<160> NUMBER OF SEQ ID NOS: 11

<210> SEQ ID NO 1
<211> LENGTH: 624
<212> TYPE: DNA
<213> ORGANISM: Pectinatus frisingensis

<400> SEQUENCE: 1
gaagtcgtaa caaggtagcc gtatcggaag gtgcggctgg atcacctcct ttctaaggat    60
taaaacaatc cgtcgagcac atccggaaca tgtattgttt ggttttgagg gtttctccct   120
caaaaaaata gatagaacta atggggggcgt agctcagctg ggagagcacc tgccttgcaa   180 gcaggggggtc aggagttcaa atctcctcgt ctccaccaga agagaaatgg gcctatagct   240
cagctggtta gagcgcacgc ctgataagcg tgaggtcagt agttcaagtc tacttaggcc   300
caccataatt gcacattgaa aactacacag aagaaaagca aagaacaatt aatcaccaat   360
gccaaacttg tgagaggaga ttttcaagag gatggcgggg aatagttgga ccaagcacaa   420
ttaggaaact aaaaacaagc taagacaaaa catataaact taagctaaag gtgatattct   480
ggaggagact cgagaatata ataaacttac cagaagcgtt cagatgcaag gaagcatgaa   540
agcgaatgaa gaaggcgtat tagtatacgc cgatgagtga gctgaaatga tgacgaagca   600
gatgagcggt tatggaaagt ttaa                                            624

<210> SEQ ID NO 2
<211> LENGTH: 442
<212> TYPE: DNA
<213> ORGANISM: Pectinatus frisingensis

<400> SEQUENCE: 2
gaagtcgtaa caaggtagcc gtatcggaag gtgcggctgg atcacctcct ttctaaggat    60
taaaacaatc cgtcgagcac atccggaaca tgtattgttt ggttttgagg gtttctccct   120
caaatattgc acattgaaaa ctacacagaa gaaaagcaaa gaacaattaa tcaccaatgc   180
caaacttgtg agaagagatt ttcaagagga tggcggggaa tagttggacc aagcacaatt   240

```
aggaaactaa aaacaagcta agacaaaaca tataaactta agctaaaggt gatattctgg    300
aggagactcg agaatataat aaacttacca gaagcgttca gatgcaagga agcatgaaag    360
cgaatgaaga aggcgtatta gtatacgccg atgagtgagc tgaaatgatg acgaagcaga    420
tgagcggtta tggaaagttt aa                                             442

<210> SEQ ID NO 3
<211> LENGTH: 724
<212> TYPE: DNA
<213> ORGANISM: Pectinatus cerevisiiphilus

<400> SEQUENCE: 3
gaagtcgtaa caaggtagcc gtatcggaag gtgcggctgg atcacctcct ttctaaggat     60
ttgacaaaaa tctgtcgagt acatccggaa tatgtattgt ttggttttga gggtttctcc    120
ctcataaata tatagtagat acttgtaaga gtgtttatgg tatgtttaaa agctggtcgg    180
aaatattgtg gtgcaaaaaa atgcatggca gtagagaaga ctggtaaaaa agaatgaac    240 taatggggc gtagctcaga tgggagagca cctgccttgc aagcaggggg tcaggagttc    300
aactctcctc gtctccacca gaagagaaag ggcctatagc tcagctggtt agagcgcacg    360
cctgataagc gtgaggtcag tagttcaagt ctacttaggc ccaccaatat tgcacattga    420
aaactacaca gaagaaagca agaacaatt atcaccaatg ccaaacttgt aagagaaatc    480
gaggagagaa tggcggggaa tagttggacc aagcacaaat taggaaaaga aacaaacgct    540
aagaaacaaa catataaact taagcgaaaa ggtgatattc tggaggaaac ttcagagtat    600
ataaacttac cagaagcgtt cagatgcgag gaagggcaaa gctgagagaa gaaagcgtat    660
taatatacgc tgatgaacga agcaaagcac tgacaaagca gatggatggt tatgggaagt    720
taca                                                                 724

<210> SEQ ID NO 4
<211> LENGTH: 399
<212> TYPE: DNA
<213> ORGANISM: Pectinatus cerevisiiphilus

<400> SEQUENCE: 4
gaagtcgtaa caaggtagcc gtatcggaag gtgcggctgg atcacctcct ttctaaggat     60
ttgacaaaaa tctgtcgagt acatccggaa tatgtattgt ttggttttga gggtttctcc    120
ctcataaata ttgcacattg aaaactacac agaagaaagc aaagaacaat tatcaccaat    180
gccaaacttg taagagaaat cgagaagaga atggcgggga atagttggac caagcacaaa    240
ttaggaaaag aaacaaacgc taagaaacaa acatataaac ttaagcgaaa aggtgatatt    300
ctggaggaaa cttcagagta tataaactta ccagaagcgt tcagatgcga ggaagggcaa    360
agcactgaca agtagatgg atggttatgg gaagttaca                            399

<210> SEQ ID NO 5
<211> LENGTH: 19
<212> TYPE: DNA
<213> ORGANISM: Pectinatus frisingensis

<400> SEQUENCE: 5
ccatcctctt gaaaatctc                                                  19

<210> SEQ ID NO 6
<211> LENGTH: 20
<212> TYPE: DNA
<213> ORGANISM: Pectinatus frisingensis
```

```
<400> SEQUENCE: 6
tctcrtctca caagtttggc                                          20

<210> SEQ ID NO 7
<211> LENGTH: 19
<212> TYPE: DNA
<213> ORGANISM: Pectinatus cerevisiiphilus

<400> SEQUENCE: 7
cactcttaca agtatctac                                           19

<210> SEQ ID NO 8
<211> LENGTH: 20
<212> TYPE: DNA
<213> ORGANISM: Pectinatus cerevisiiphilus

<400> SEQUENCE: 8
ccacaatatt tccgaccagc                                          20

<210> SEQ ID NO 9
<211> LENGTH: 20
<212> TYPE: DNA
<213> ORGANISM: Pectinatus cerevisiiphilus

<400> SEQUENCE: 9
agtcttctct actgccatgc                                          20

<210> SEQ ID NO 10
<211> LENGTH: 20
<212> TYPE: DNA
<213> ORGANISM: Pectinatus frisingensis

<400> SEQUENCE: 10
cgtatccaga gatggatatt                                          20

<210> SEQ ID NO 11
<211> LENGTH: 20
<212> TYPE: DNA
<213> ORGANISM: Pectinatus cerevisiiphilus

<400> SEQUENCE: 11
cgtatgcaga gatgcatatt                                          20
```